(12) United States Patent
Binder et al.

(10) Patent No.: US 6,435,388 B1
(45) Date of Patent: Aug. 20, 2002

(54) APPARATUS AND METHODS FOR DONNING STERILE GLOVES

(76) Inventors: Kurwin J. Binder, 10821 W. Quail Ave., Sun City, AZ (US) 85373; Leon E. McCrary, 63 Old Forge Rd., Scituate, MA (US) 02066; Edward Jordan, 3 Satucket Rd., Rockland, MA (US) 02370

( * ) Notice: Subject to any disclaimer, the term of this patent is extended or adjusted under 35 U.S.C. 154(b) by 0 days.

(21) Appl. No.: 09/916,413

(22) Filed: Jul. 26, 2001

Related U.S. Application Data

(60) Provisional application No. 60/244,026, filed on Oct. 27, 2000.

(51) Int. Cl.[7] ............................................. A47G 25/80
(52) U.S. Cl. ...................................................... 223/111
(58) Field of Search ........................... 223/111–120, 78, 223/79; 294/3.6

(56) References Cited

U.S. PATENT DOCUMENTS

| | | | |
|---|---|---|---|
| 1,938,685 A | | 12/1933 | Breuls et al. ............... 223/20.2 |
| 1,996,377 A | | 4/1935 | Hinchen ..................... 223/20.2 |
| 3,695,493 A | | 10/1972 | Karr ............................ 223/111 |
| 4,889,266 A | * | 12/1989 | Wight ........................ 223/111 |
| 4,915,272 A | * | 4/1990 | Vlock ........................ 223/111 |
| 5,058,785 A | * | 10/1991 | Rich et al. ................. 223/111 |
| 5,078,308 A | | 1/1992 | Sullivan ..................... 223/111 |
| 5,868,290 A | * | 2/1999 | Green, Sr. et al. ......... 223/111 |
| 6,053,380 A | * | 4/2000 | Sherrod et al. ............ 223/111 |

* cited by examiner

*Primary Examiner*—Bibhu Mohanty
(74) *Attorney, Agent, or Firm*—Foley, Hoag & Eliot, LLP

(57) ABSTRACT

The present invention is directed to glove inflation apparatuses and methods for donning sterile gloves. The apparatuses includes at least one vacuum chamber that has an opening sized and shaped for receiving a glove and for establishing a fluid-tight seal between the glove and the vacuum chamber. The apparatuses further includes a vacuum pump which is connected to the chamber and a source of compressed gas which is in fluid communication with the glove. The apparatuses further includes a switch that is connected to the pump and the source of compressed gas. The switch has two states. In the first state, the switch permits the pump to evacuate the chamber. In the second state, the switch permits the source of compressed gas to expel the glove from the opening of the chamber. The methods for donning a sterile glove include the steps of securing a cuff portion of a glove onto an opening of a vacuum chamber to establish a fluid-tight seal between the glove and the vacuum chamber, creating a vacuum in the vacuum chamber so as to inflate the glove, placing a hand in the inflated glove, and applying positive pressure to the cuff portion of the glove to release the glove from the opening of the vacuum chamber.

17 Claims, 9 Drawing Sheets

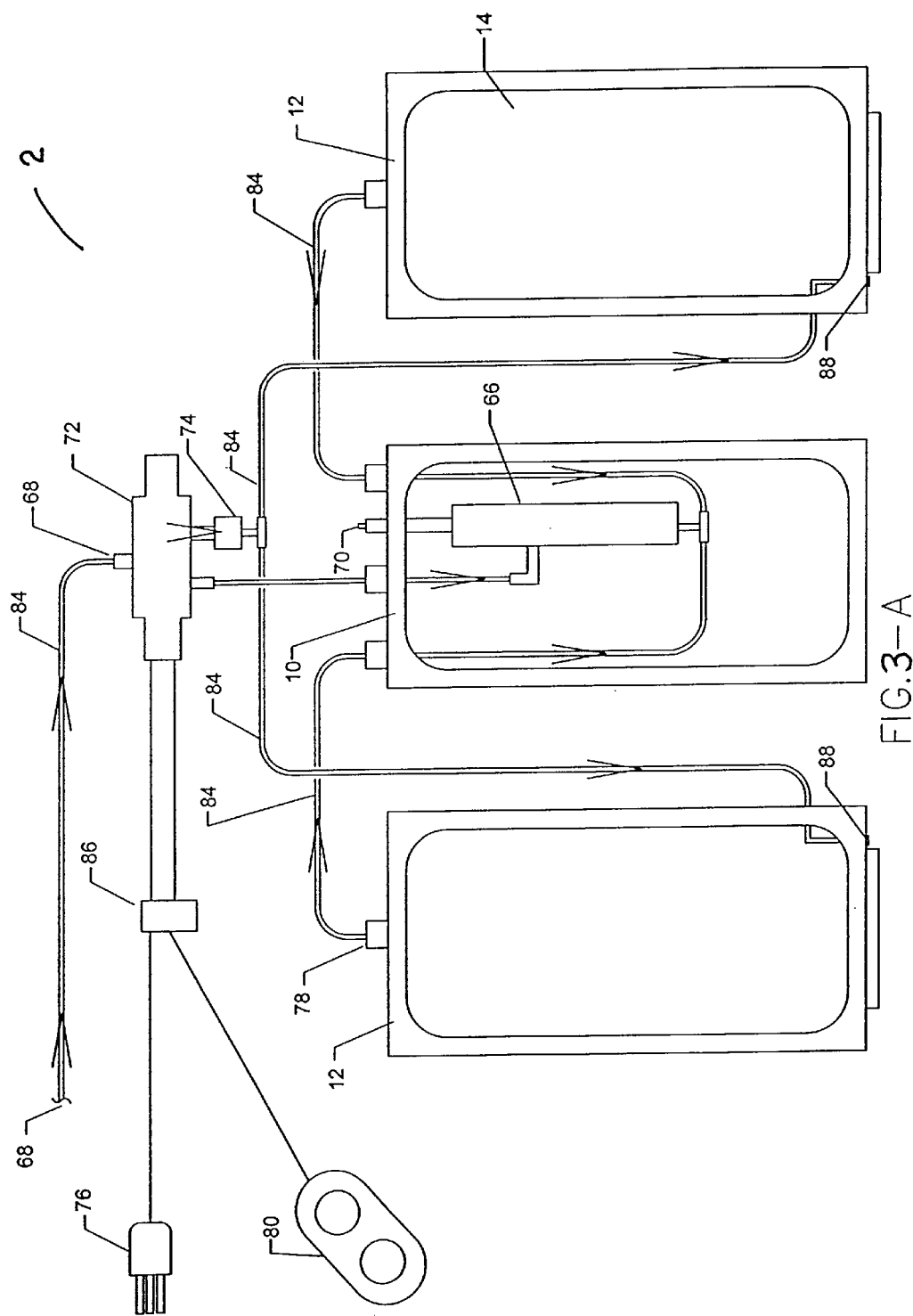

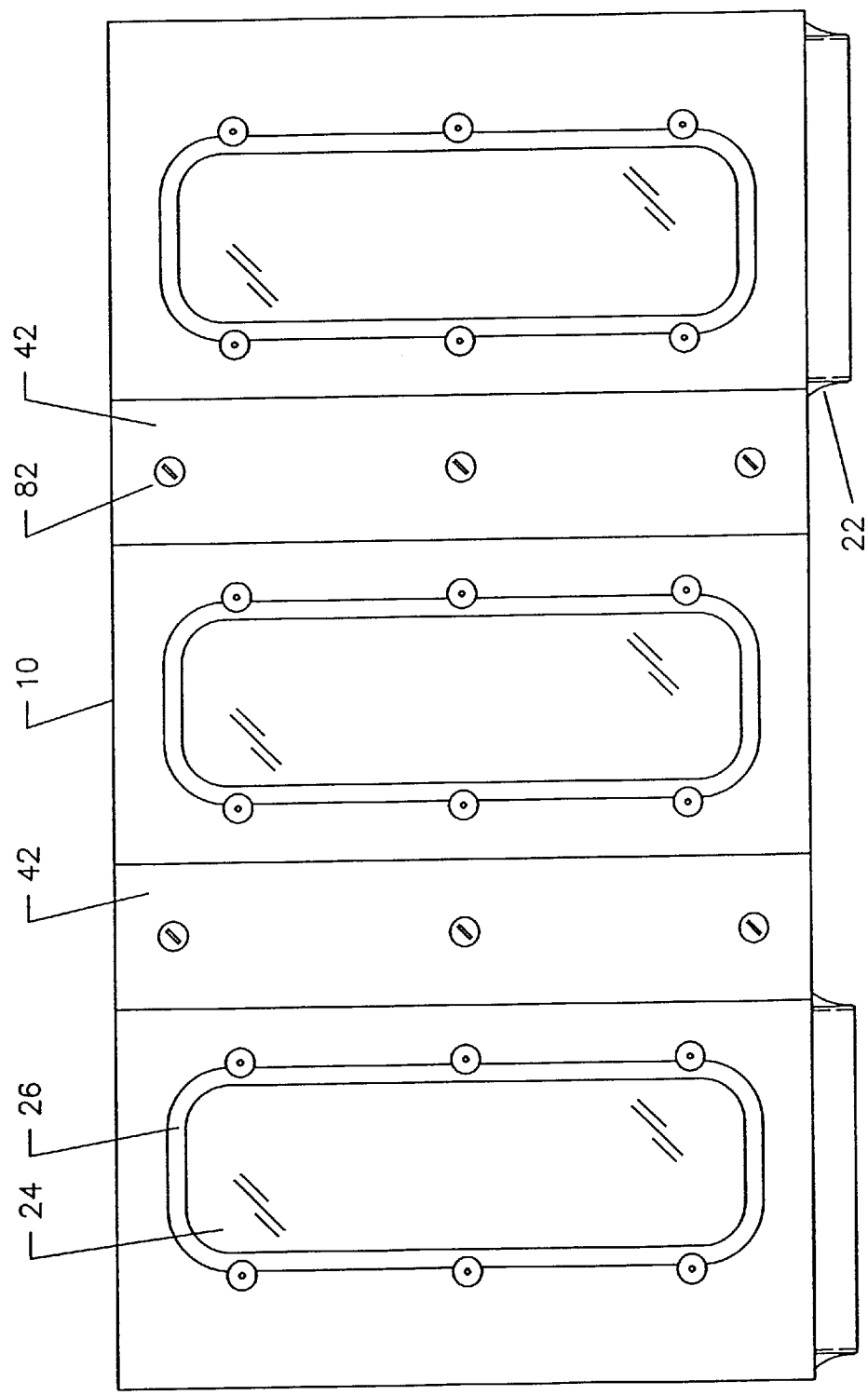
FIG. 3-B

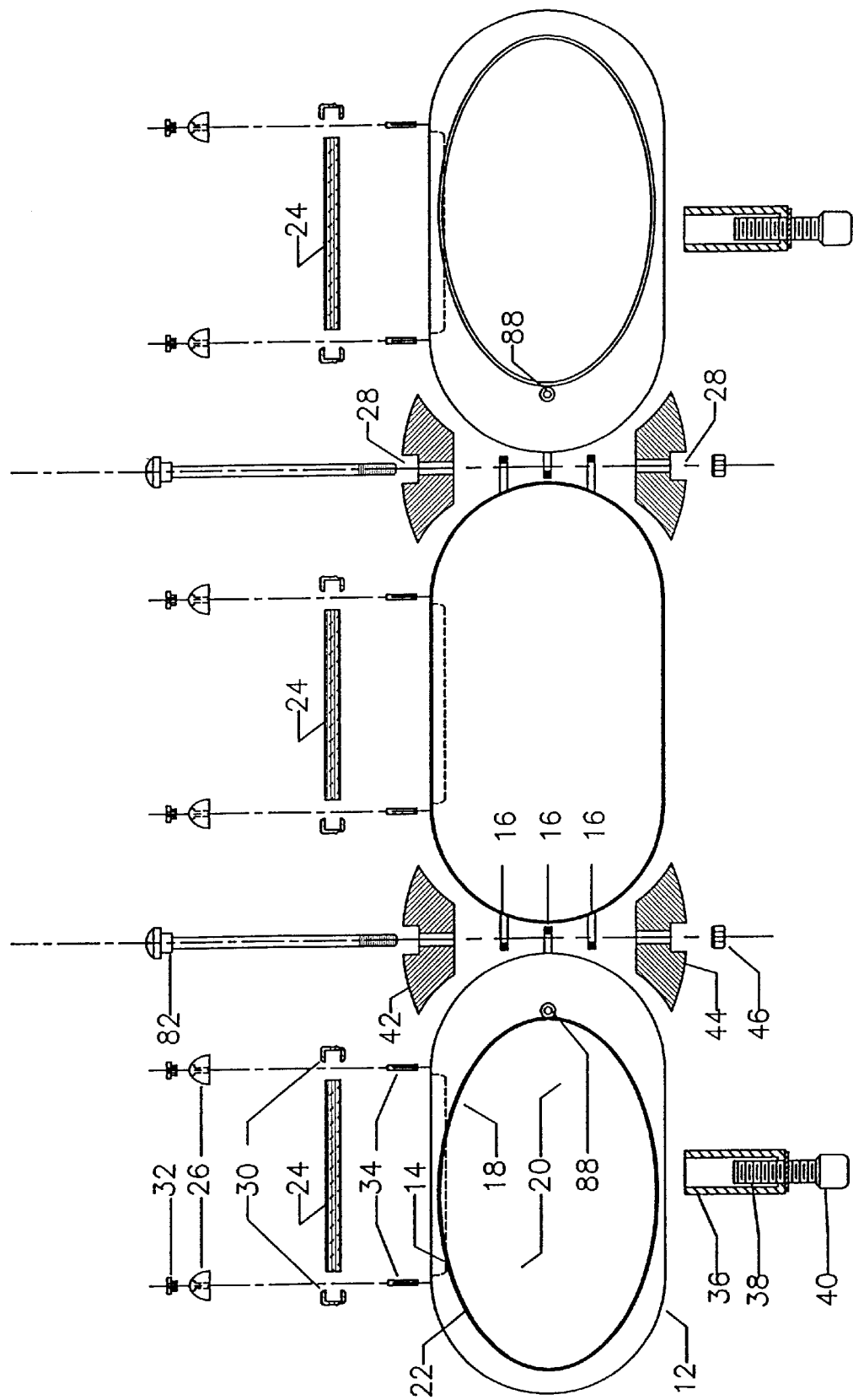
FIG. 4-A

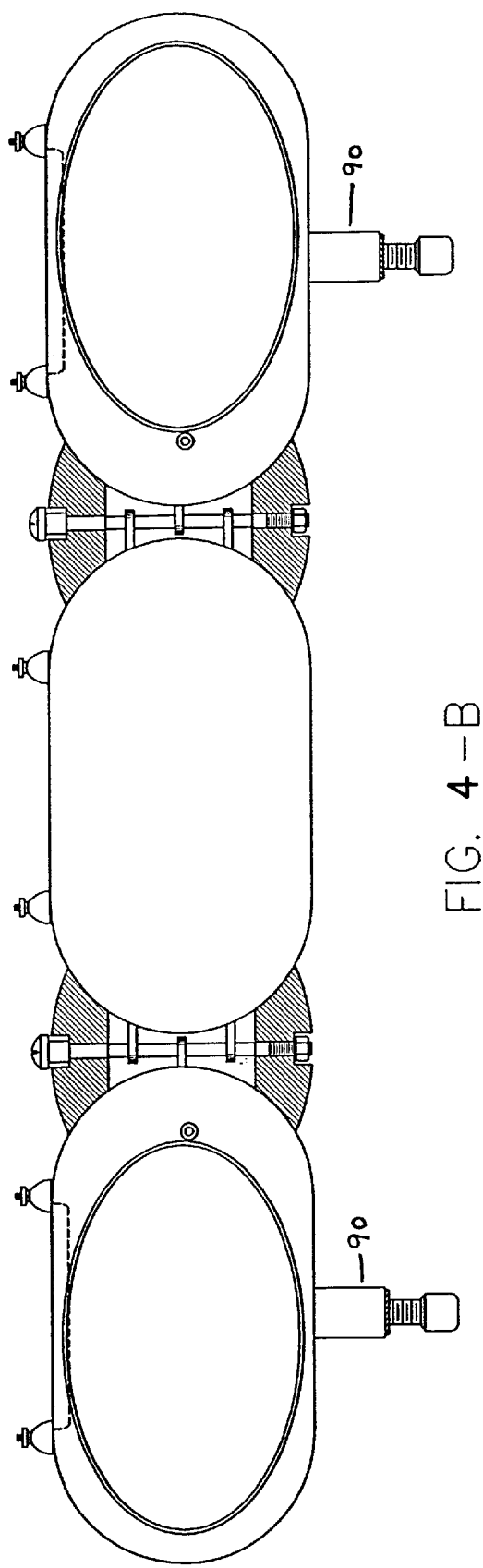

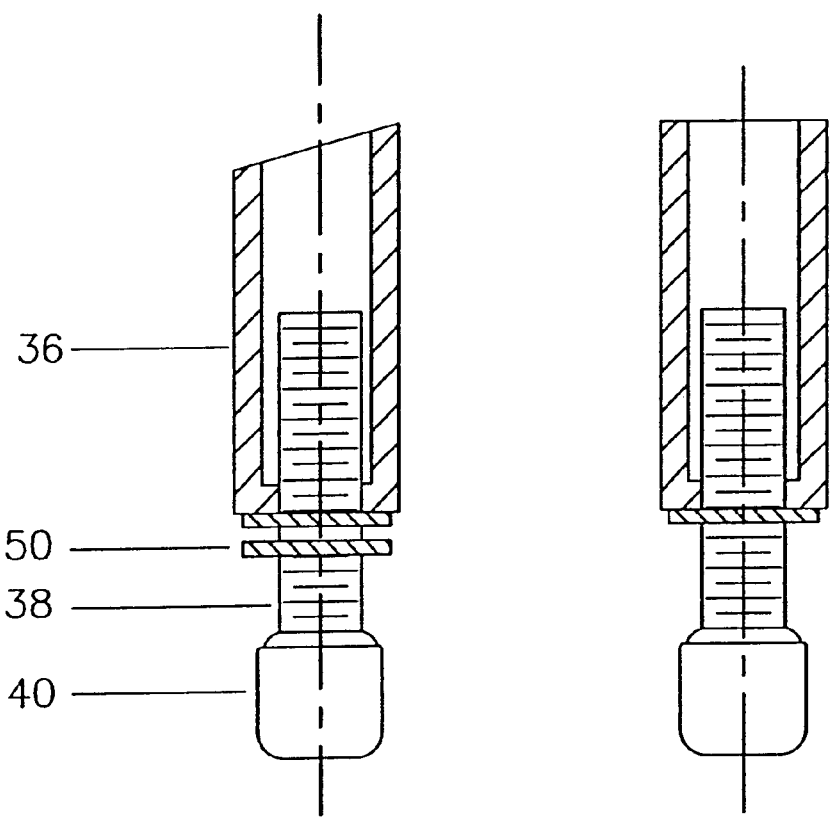
FIG. 7-A  FIG. 7-B

US 6,435,388 B1

APPARATUS AND METHODS FOR DONNING STERILE GLOVES

CROSS-REFERENCE TO RELATED APPLICATIONS

This application claims priority to U.S. Provisional Patent Application No. 60/244,026, filed Oct. 27, 2000, the contents of which are herein incorporated by reference.

FIELD OF THE INVENTION

This invention relates in general to the field of vacuum technology and in particular to devices and methods that use vacuum principles to ensure the sterility of surgical gloves.

BACKGROUND OF THE INVENTION

Surgical gloves are worn in a variety of environments that demand a very high degree of sterility, for example, the medical, food-preparation and manufacturing "clean room" environments. In the medical environment, surgical gloves are worn to prevent the hands of a doctor or a surgeon from contacting a patient's body during a physical examination or a surgical operation. Wearing non-sterile surgical gloves in such an environment can lead to infection of the patient. In the "clean room" environment, surgical gloves are worn to prevent the hands of a technician from contacting wafers and other devices supporting highly sensitive electronic circuits. Wearing non-sterile gloves in such an environment can lead to contamination of the wafers and other devices, making them unsuitable for fabrication.

Typically, surgical gloves are manufactured to be sterile. This sterility can be adversely affected, however, by manufacturing defects, such as rips, tears, and holes in the glove fabric. Such manufacturing defects are not always visible to the naked eye. This sterility can also be adversely affected during the process in which the wearer puts on the surgical gloves. During this process, oils and other fluids on the hands can contact and contaminate the exterior surface of the gloves. Ordinarily, the risk of undesirable contamination in this process is reduced by having an assistant fit the surgical gloves over the hands of the wearer.

Conventional devices for determining whether manufacturing defects exist in a surgical glove are inaccurate and difficult to use. Moreover, conventional devices do not circumvent the need for an assistant to reduce the risk of contamination during the process in which the gloves are fitted to the hands of the wearer.

SUMMARY OF THE INVENTION

The present invention is directed to glove inflation apparatuses that can utilize both a vacuum source and a compressed gas source to accurately determine whether manufacturing defects exist in a pair of surgical gloves and to fit a surgical glove onto a hand in a manner ensuring a high degree of sterility without the need for outside assistance.

In accordance with one aspect of the present invention, a glove inflation apparatus includes at least one vacuum chamber that has an opening sized and shaped for receiving a glove and for establishing a fluid-tight seal between the glove and the vacuum chamber. The apparatus further includes a vacuum source which is connected to the chamber and a source of compressed gas which is in fluid communication with the glove. The apparatus further includes a switch that is connected to the vacuum source and the source of compressed gas. The switch has two states. In the first state, the switch permits the pump to evacuate the chamber. In the second state, the switch permits the source of compressed gas to expel the glove from the opening of the chamber.

In accordance with another aspect of the invention, the glove inflation apparatus can have both a first vacuum chamber and a second vacuum chamber. The first vacuum chamber can have an opening sized and shaped for receiving a first glove, and the second vacuum chamber can have an opening sized and shaped for receiving a second glove.

In accordance with a further aspect of the present invention, the glove inflation apparatus can include a controller connected to the switch. The controller can be a foot pedal or any other electrical or mechanical device which is suitable for controlling the switch.

In accordance with another aspect of the present invention, the vacuum chamber of the glove inflation apparatus can include a transparent portion to facilitate viewing of the glove while the glove is secured onto the opening of the vacuum chamber.

In accordance with another aspect of the present invention, the glove inflation apparatus can include a nozzle and a support ring sized and shaped to engage the opening of the vacuum chamber. The nozzle preferably directs the delivery of the compressed gas to the glove.

In accordance with a further aspect of the present invention, the glove inflation apparatus can include a glove assembly for supporting a cuff portion of a glove, a vacuum chamber that has an opening for receiving the glove assembly, a vacuum pump connected to the vacuum chamber, and a source of compressed gas connected to the glove assembly.

In accordance with another aspect of the present invention, the glove assembly of the glove inflation apparatus can include a glove, a support ring having an interior surface and an exterior surface, a nozzle, adjacent to the exterior surface of the support ring, wherein a first portion of the nozzle connects to the source of compressed gas, and wherein a second portion of the nozzle retains the glove.

In accordance with yet a further aspect of the present invention, the present invention is directed to a method for donning a sterile glove. The method comprises securing a cuff portion of a glove onto an opening of a vacuum chamber, generating a vacuum in the vacuum chamber to inflate the glove, placing a hand in the inflated glove and applying positive pressure to the cuff portion of the glove to release the glove from the opening of the vacuum chamber.

Further features and advantages of the present invention will become apparent from the following description of the preferred embodiment and from the claims.

BRIEF DESCRIPTION OF THE DRAWINGS

FIG. 3a is a schematic view of a glove inflation apparatus constructed according to the present invention;

FIG. 3b is a more detailed illustration of the vacuum chambers for use in the apparatus shown in FIG. 3a;

FIG. 4a is a schematic view in exploded cross-section of the apparatus shown in FIG. 3a;

FIG. 4b is an assembled view of the apparatus shown in FIG. 4a;

FIGS. 7a and 7b are schematic views of the adjustable supports of the apparatus shown in FIG. 3a.

DETAILED DESCRIPTION OF EXEMPLARY EMBODIMENTS

Figure 1:
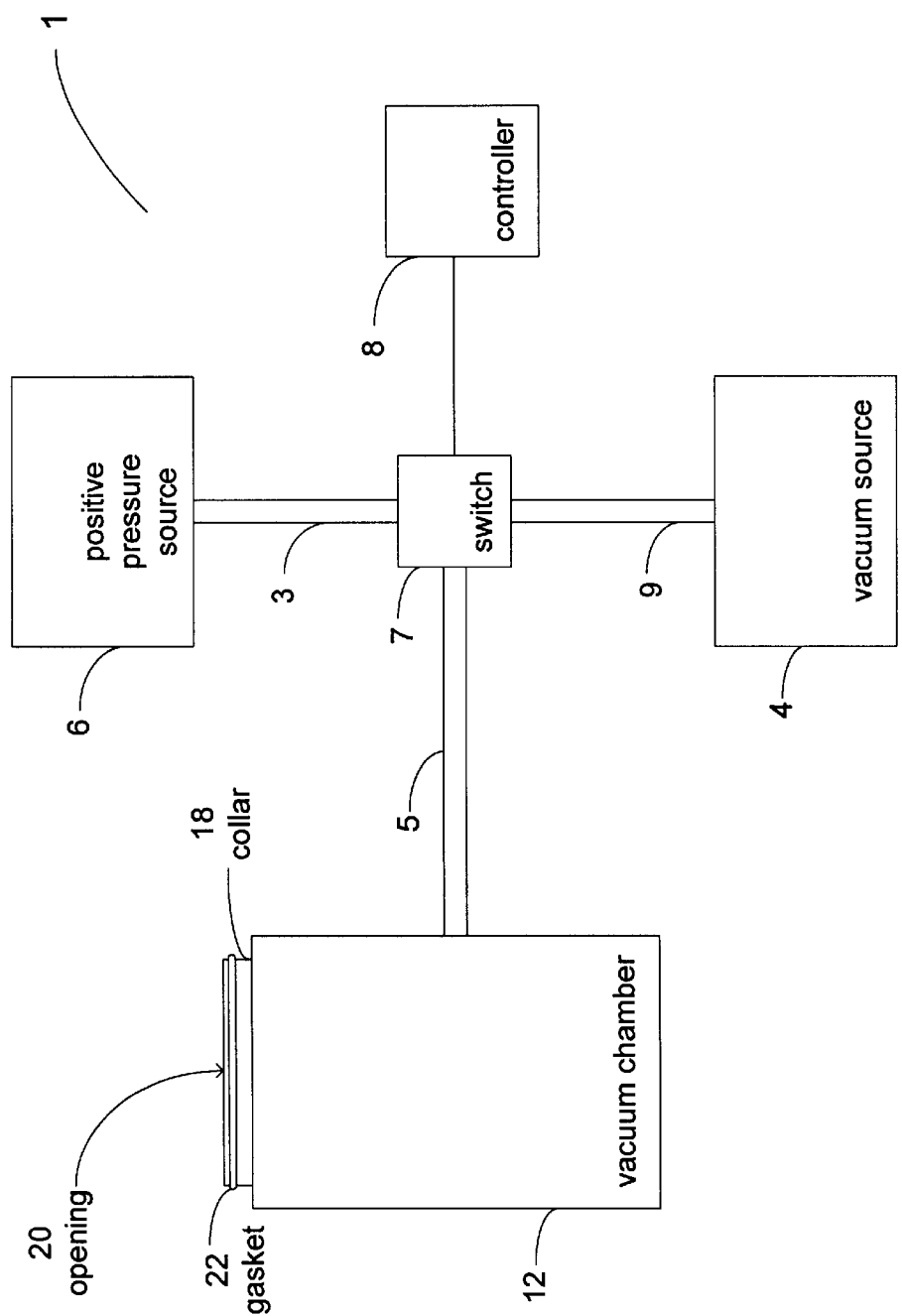
FIG. 1 is a schematic view of a glove inflation apparatus constructed according to the present invention.

An exemplary embodiment of a glove inflation apparatus 1 constructed according to the present disclosure is shown in FIG. 1. The glove inflation apparatus 1 can be used to accurately determine whether a surgical glove contains any defects. The apparatus 1 can also be used to fit a surgical glove onto the hand of a wearer in a manner ensuring a high degree of sterility without the need for outside assistance. The apparatus 1 includes a vacuum chamber 12, a vacuum source 4, a positive pressure source 6, a switch 7 and a controller 8. As shown in FIG. 1, the vacuum source 4 is connected to (i.e., in fluid communication with) the vacuum chamber 12 via tubes 5 and 9 and the switch 7. The vacuum source 4 can be a vacuum pump or a remotely-located vacuum reservoir. The source of compressed gas 6 is connected to the vacuum chamber 12 via tubes 3 and 5 and the switch 7. The pressure within the vacuum chamber 12 is regulated by the switch 7 which is controlled, e.g., electrically or mechanically, by the controller 8. The switch 7 of FIG. 1 can be an automatic or manually-controlled three-way control valve.

As shown in FIG. 1, vacuum chamber 12 has an opening 20 defined by a protruding collar 18 for receiving a glove assembly (described below). The opening 20 is sized and shaped for receiving a glove, and more specifically, the cuff portion of a glove. When the apparatus 1 is used to fit a surgical glove onto the hand of a wearer, the opening 20 must be sized and shaped to also allow the wearer's hand to fit through the opening 20. Collar 18 is surrounded by a gasket 22. The gasket 22, which may be an O-ring, a flat gasket, a tapered gasket or any other suitable type of gasket device, may be seated within a channel, i.e., a groove (not shown) manufactured into the collar 18.

Figure 2:
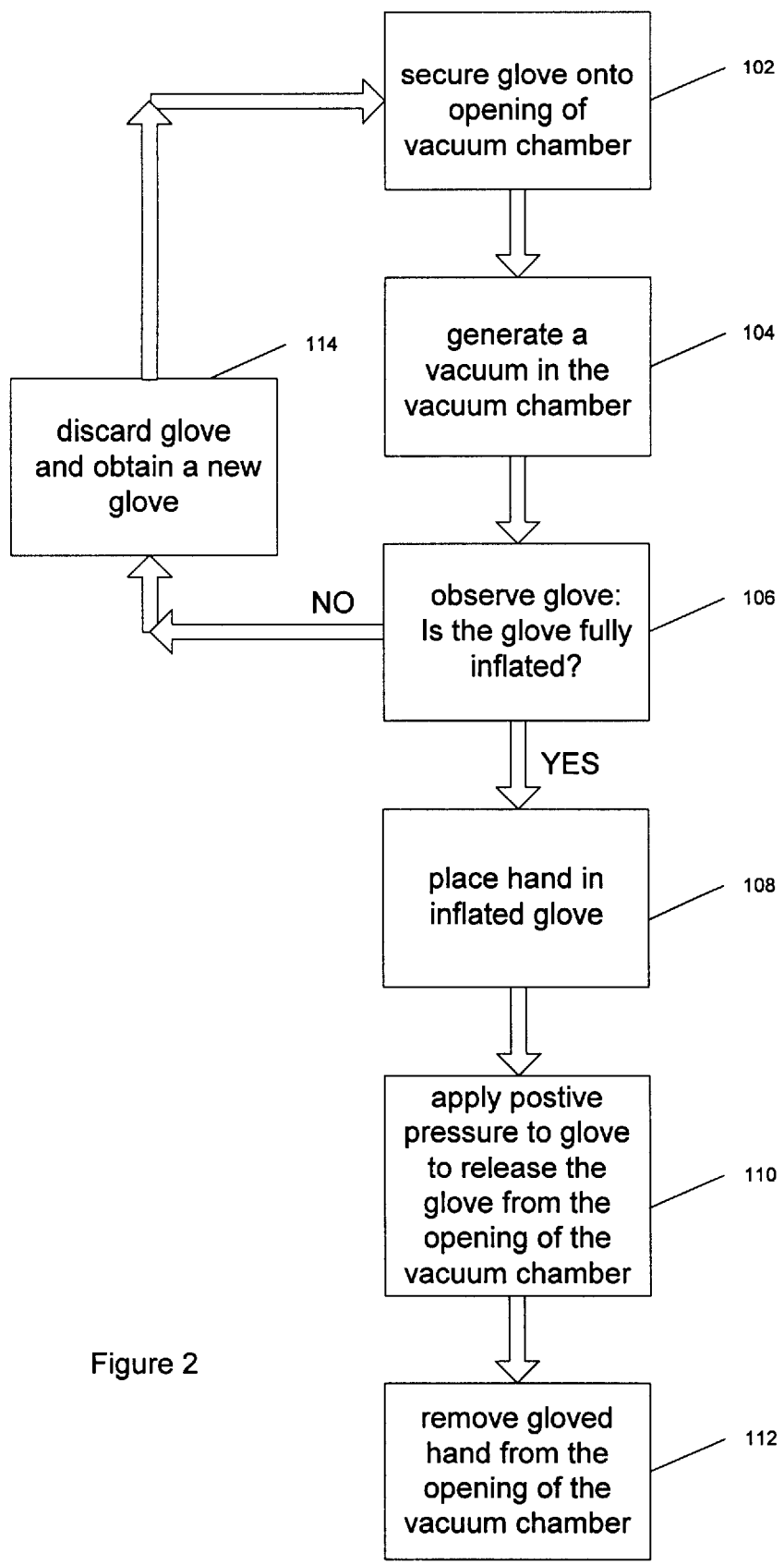
FIG. 2 is a flow-chart diagram illustrating a method for donning a glove according to the present invention.

Operation of the glove inflation apparatus 1 will be described in connection with FIG. 2 which illustrates an exemplary method for donning a sterile glove in accordance with the present disclosure. The cuff portion of a glove 100 (see FIG. 5) is secured onto the opening 20 of a vacuum chamber 12 to establish a fluid-tight seal between the glove 100 and the vacuum chamber 12, step 102. A vacuum is then generated in the vacuum chamber 12 by operation of the vacuum source 4, switch 7 and controller 8, step 104. The vacuum generated in the vacuum chamber 12 needs to be controlled, i.e., set at an appropriate level, such that the fluid-tight seal established between the glove 100 and the vacuum chamber 12 does not get compromised, and such that the glove 100 does not get over inflated. Over inflation of the glove 100 may detrimentally affect the integrity of the glove 100's material.

If the glove 100 is free of defects, i.e., there are no holes or tears in the glove, and a fluid-tight seal between the glove 100 and the vacuum chamber 12 has been established, the negative pressure in the vacuum chamber 12 will cause the secured glove 100 to inflate. Once a vacuum has been established, the operator (who may or may not be the same person who shall ultimately wear the glove) then verifies the integrity of glove 100 by observing whether the glove 100 has fully inflated or not, step 106. If there are perforations, tears or holes in the glove 100, the glove 100 will not inflate, or will only partially inflate. If the glove 100 fails to fully inflate, the glove 100 is removed from the opening 20 of the vacuum chamber 12 and discarded, step 114. If the glove 100 fully inflates, the hand (to be gloved) is placed within the inflated glove 100, step 108. Positive pressure is then applied to the cuff portion of the glove 100 to release the glove 100 from the opening 20 of the vacuum chamber 12, step 110. The amount of positive pressure necessary to cause the glove 100 to be released from the opening 20 will depend upon the type of glove used and the manner in which the glove 100 is secured onto the opening 20 of the vacuum chamber 12. For most types of readily-available surgical gloves, a positive pressure of at least eight (8) p.s.i. can be sufficient to release the glove 100 from the opening 20. Finally, the gloved hand is removed from the opening 20 of the vacuum chamber 12, step 112.

An alternate embodiment of a glove inflation apparatus 2 constructed according to the present disclosure is shown in FIG. 3a. The glove inflation apparatus 2 can be used to accurately determine whether a pair of surgical gloves contains any defects. The apparatus 2 can also be used to fit a pair of surgical gloves onto the hands of a wearer in a manner ensuring a high degree of sterility without the need for outside assistance. The apparatus 2 includes two vacuum chambers 12. Each vacuum chamber 12 has a cutout 14 in its top surface. As shown in FIGS. 3b and 4a, each cutout 14 is suitably sized and shaped to receive a transparent cover 24 surrounded by a gasket 30. The cover 24 and the gasket 30 are assembled to the vacuum chamber 12 so as to create a fluid-tight seal. Stud screws 34, keepers 26, and lugs 32 are used to secure the cover 24 and the gasket 30 to the vacuum chambers 12.

As also shown in FIG. 3a, the apparatus 2 includes a pump chamber 10. Located within the pump chamber 10 is a vacuum pump 66 having an outlet port 70. Like the vacuum chambers 12, the pump chamber also has a cutout 14 in its top surface for receiving a transparent cover 24 surrounded by a gasket 30. Assembly of the cover 24 to the pump chamber 10 follows the technique described above for assembling the cover 24 to the vacuum chamber 12.

As shown in FIGS. 3b, 4a, and 4b, the vacuum chambers 12 and the pump chamber 10 are physically connected to each other. This connection is accomplished by first inserting bolts 82 through upper stiles 42 and lower stiles 44 having receiving bores 28 and later securing the bolts 82 with nuts 46. Clevises 16 are also used to physically connect the chambers in the manner indicated in FIGS. 4a and 4b.

As shown in FIGS. 3a, 3b, and 4a, each vacuum chamber 12 has an opening 20 defined by a protruding collar 18. Each collar 18 is surrounded by a gasket 22. The gasket 22, while shown to be a tapered gasket, can be an O-ring, a flat gasket, a tapered gasket or any other suitable type of gasket device. Also, gasket 22 can be seated within a channel (not shown) manufactured into the collar 18.

As further shown in FIG. 3a, the vacuum pump 66 and the pump chamber 10 are connected to the vacuum chambers 12 via tubes 84 which pass through bulkhead fittings 78. The vacuum pump 66 and the pump chamber 10 are also connected via a tube 84 to a switch 72 having a control valve 74. The vacuum chambers 12 are connected to each other via tubes 84 which pass through the control valve 74 and enter grommets 88. A source of compressed gas (not shown) is connected to the switch 72 via a tube 84 that enters through an inlet port 68. The switch 72 is electrically connected to a junction box 86, and the junction box 86 is electrically connected to a power supply 76 and a foot pedal 80 having two chambers.

As shown in FIGS. 4a, 4b, 5, 7a, and 7b, the apparatus 2 rests upon a pair of adjustable supports 90 located underneath the vacuum chambers 12. The supports 90 comprise legs 38, pivoting feet 40, leg passages 36, and locking nuts 50. Alternatively, in other embodiments constructed in accordance with the present invention, additional adjustable supports can be used.

Figure 5:
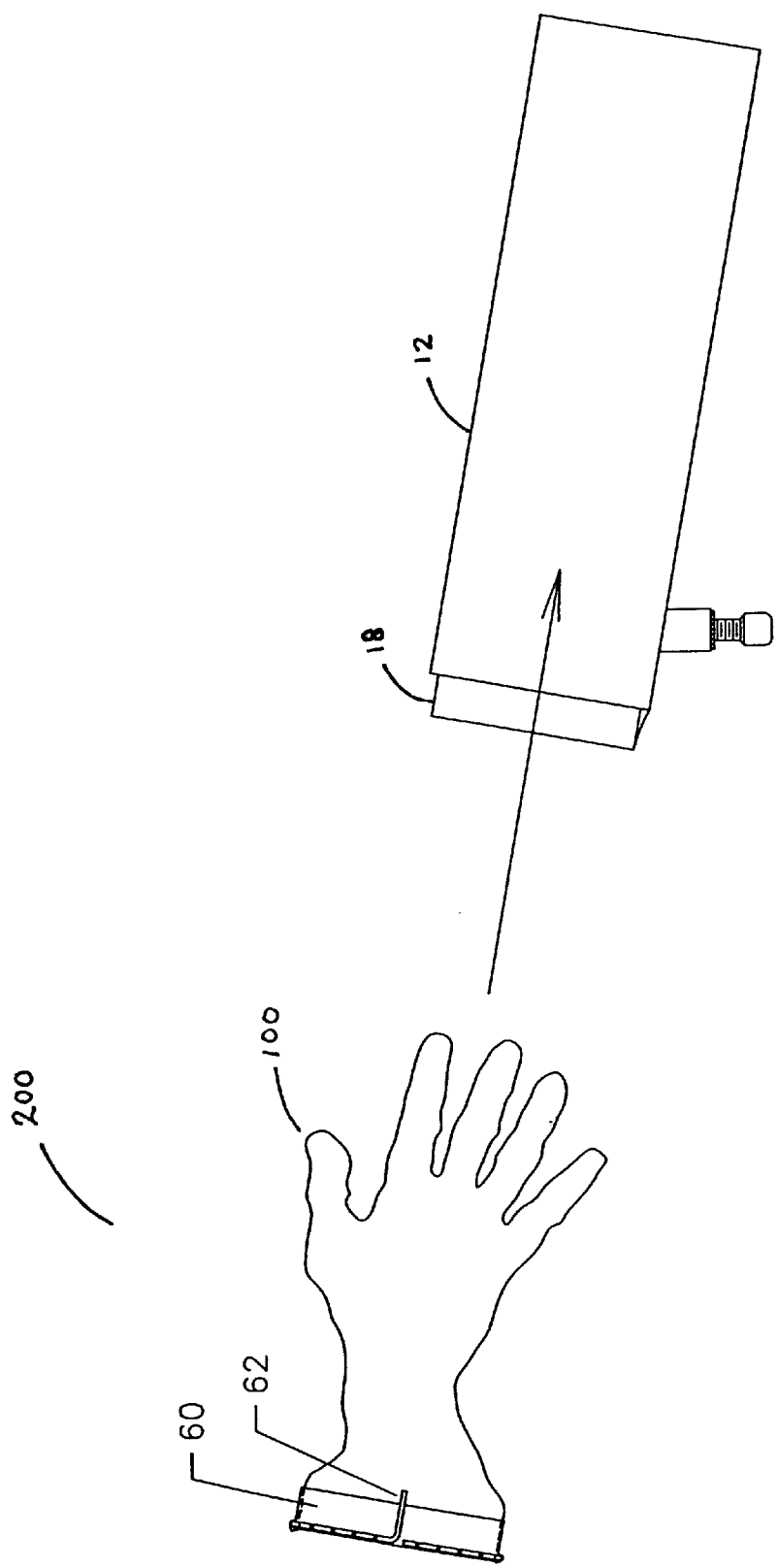
FIG. 5 is a schematic view of the apparatus shown in FIG. 3a illustrating the insertion of a glove assembly into the apparatus.
Figure 6:
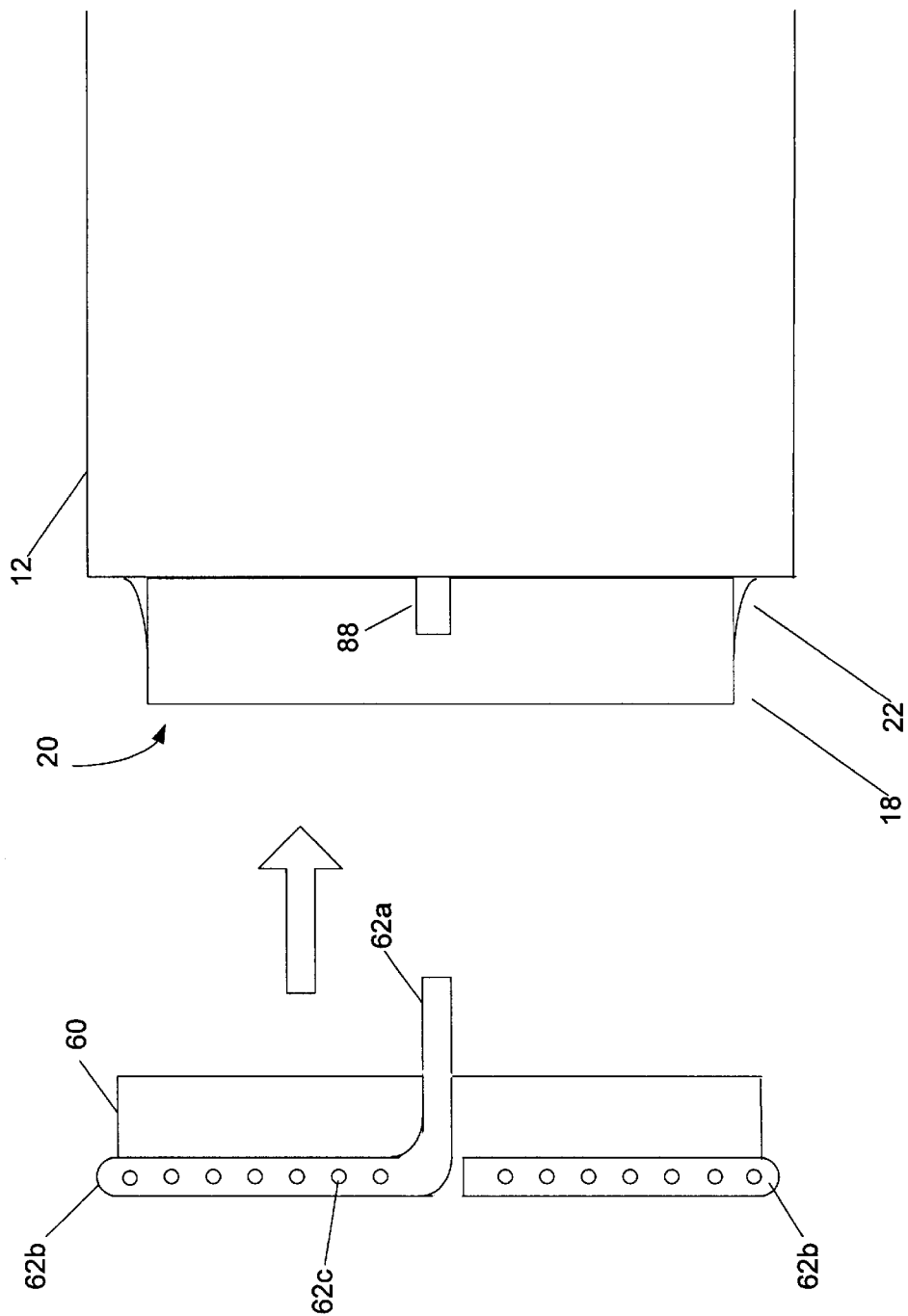
FIG. 6 is a side view of a support ring, nozzle and a vacuum chamber.

As illustrated in FIGS. 5 and 6, the support ring 60 and nozzle 62 are sized and shaped to engage the opening 20 of the chamber 12. The support ring 60 has an interior surface and an exterior surface. The nozzle 62, which is coupled to the exterior surface of the support ring 60, has a first portion 62a which connects to the source of compressed gas, e.g., via grommet 88, and a second portion 62b for retaining the glove 100. The nozzle 62 can be bonded to the support ring 60 via traditional bonding, welding, and/or brazing techniques or any other suitable techniques which are well known to those skilled in the art. Alternatively, the nozzle 62 and the support ring 60 can be of an unitary construction. In other words, nozzle 62 and support ring 60 can be manufactured as a single component. The nozzle 62 and the support ring 60 can be made of plastic, metal or any other suitable material.

The glove 100 (not shown in FIG. 6 for sake of clarity) is placed within the interior surface of the support ring 60 and the opening of the glove 100 (i.e., the cuff portion of the glove) can be stretched over the retaining portion 62b of the nozzle 62 to secure the glove 100 to the nozzle 62. The resiliency of the material used in the glove 100, when stretched over the retaining portion 62b of the nozzle 62, can aid in securing the glove 100 to the opening 20 of the vacuum chamber 12. Also, surgical gloves often have a bead (or lip) of material along the opening of the glove 100. The glove 100's bead, when pulled over the retaining portion 62b of the nozzle 62, can further aid in securing the glove 100 to the opening 20 of the vacuum chamber 12. Nozzle 62 has a series of small holes 62c, i.e. orifices, located along the retaining portion 62b of the nozzle 62 which can direct the delivery of the compressed gas to the glove 100 once the first portion 62a of the nozzle 62 has been connected to the source of compressed gas.

Once the glove 100 is installed onto the support ring 60-nozzle 62 assembly, the glove assembly 200—consisting of the glove 100, support ring 60 and the nozzle 62—is then placed onto the collar 18 of the vacuum chamber 12 with the first portion 62a of the nozzle 62 connected to the source of compressed gas. For ease of operation, the glove assembly 200 can be manufactured as a pre-assembled package that is to be used with the glove inflation apparatuses disclosed herein. Alternatively, the support ring 60-nozzle 62 assembly can be mated with the opening 20 of the vacuum chamber 12 prior to installing the glove 100 onto the support ring 60-nozzle 62 assembly.

The frictional forces present between the collar 18, gasket 22 and the support ring 60 can be sufficient to hold the support ring 60-nozzle 62 assembly to the collar 18 when the glove inflation apparatus of the present disclosure is in use. Alternatively, however, mechanical locking devices or fasteners such as spring loaded bearing mechanisms or mechanical latches can utilized to secure the support ring 60-nozzle 62 assembly to the collar 18. Gasket 22, located between the collar 18 and the interior surface of the support ring 60, ensures that a fluid-tight seal is exists between the support ring 60 and the collar 18. At this point, the vacuum chamber 12 is a fluid-tight compartment, provided that the glove 100 is free from any defects (manufacturing or otherwise) such as rips, tears, or holes.

As discussed above, the apparatus 2 has two stages of operation—a vacuum pumping stage, and a positive pressure stage. The directions of fluid flow through the tubes 84 during these two stages of operation are indicated by arrows in FIG. 3a.

Referring to FIG. 3a again, once a pair of gloves 100 has been placed into the vacuum chambers 12, the operator depresses the first chamber, i.e., the first button, of the foot pedal 80 to commence the vacuum pumping stage. In response, the foot pedal 80 directs the junction box 86 to send a signal to the switch 72 to close the control valve 74. High-pressure gas then flows from the source of compressed gas (not shown) via tubes 84 through the switch 72 and into the vacuum pump 66. Subsequently, the vacuum pump 66 begins to evacuate both of the vacuum chambers 12 simultaneously, discharging gas through the outlet port 70. Provided that the gloves 100 do not have any manufacturing defects, evacuation of the vacuum chambers 12 will be accompanied by inflation of the gloves 100. This inflation can be observed through the transparent covers 24 on top of the vacuum chambers 12. If the gloves 100 do have manufacturing defects, however, the vacuum chambers 12 will not be fluid-tight. As a consequence, the vacuum pump 66 will not be able to evacuate the vacuum chambers 12, and the gloves 100 will not inflate. Observation of the inflation of the gloves 100, therefore, assures the operator that the gloves 100 are free of manufacturing defects that adversely affect sterility.

After observing the inflation of the gloves 100, the operator places his hands into the gloves 100 and waits until the fit of the gloves 100 feels comfortable. At that time, the operator depresses the second chamber of the foot pedal 80 to commence the positive pressure stage. In response, the foot pedal 80 directs the junction box 86 to send a signal to the switch 72 to open the control valve 74. High-pressure gas, preferably a sterile and clean high-pressure gas, then flows from the source of compressed gas (not shown) via tubes 84 through the control valve 74 into the grommets 88 and the nozzles 62 surrounding the support rings 60 of the gloves 100. As the high-pressure gas circulates through the support rings 60, it escapes through the small holes 62c in the nozzles 62. This burst of positive pressure blows the gloves 100 off of the support rings 60 and onto the operator's hands. The apparatus 2 thus facilitates a fitting of surgical gloves that ensures a high degree of sterility without the need for outside assistance.

The glove inflation apparatus 2 thus achieves the objects of the present invention. The apparatus 2 can be used to inflate gloves of all sizes and of both latex and non-latex composition.

The present invention has been disclosed in connection with the glove inflation apparatuses 1 and 2 shown and described in detail. Various modifications and improvements thereon will, however, become readily apparent to those skilled in the art. For example, many variations are possible on the construction of the pump chamber 10 and the vacuum chambers 12. Alternative embodiments of the present invention may be constructed without a pump chamber 10 or with a single vacuum chamber 12. The vacuum chamber 12 preferably is constructed with an observation window by which to observe the inflation of the glove 100. Many variations are also possible for the assembly of the glove 100 onto the opening 20 of the vacuum chamber 12 in a manner to create a fluid-tight seal between the glove 100 and the vacuum chamber 12. Further, many variations are possible for the mechanism by which the glove 100 is fit onto the operator's hand. The description of the glove inflation apparatuses 1 and 2 should therefore be considered only as illustrative, and not as limiting, of the present invention. The spirit and scope of the present invention is to be limited only by the following claims.

What is claimed is:

1. A glove inflation apparatus, comprising:
   at least one vacuum chamber having an opening sized and shaped for receiving a glove and for establishing a fluid-tight seal between the glove and the vacuum chamber;
   a vacuum pump connected to the chamber;
   a source of compressed gas in fluid communication with the glove; and
   a switch, connected to the pump and the source, having a first state and a second state, wherein in the first state the switch permits the pump to evacuate the chamber and further wherein in the second state the switch permits the source to expel the glove from the opening of the chamber.

2. The apparatus of claim 1, further comprising:
   a first vacuum chamber having an opening sized and shaped for receiving a first glove; and
   a second vacuum chamber having an opening sized and shaped for receiving a second glove.

3. The apparatus of claim 1, further comprising:
   a controller connected to the switch.

4. The apparatus of claim 3, wherein the controller is a foot pedal.

5. The apparatus of claim 1, wherein the chamber further comprises:
   a transparent portion.

6. The apparatus of claim 1, further comprising:
   adjustable supports for supporting the chamber.

7. The apparatus of claim 1, further comprising:
   nozzle; and
   a support ring, wherein the nozzle and support ring are sized and shaped to engage the opening of the chamber, and further wherein the nozzle directs the delivery of the compressed gas to the glove.

8. The apparatus of claim 7, wherein the nozzle and the support ring are of a unitary construction.

9. A glove inflation apparatus, comprising:
   a glove assembly for supporting a cuff portion of a glove;
   a vacuum chamber having an opening for receiving the glove assembly and for establishing a fluid-tight seal between the glove assembly and the opening of the chamber;
   a vacuum pump connected to the vacuum chamber; and
   a source of compressed gas connected to the glove assembly.

10. The glove inflation apparatus as claimed in claim 9 wherein the glove assembly comprises:
    a glove;
    a support ring having an exterior surface; and
    a nozzle, coupled to the exterior surface of the support ring, wherein a first portion of the nozzle connects to the source of compressed gas, and wherein a second portion of the nozzle retains the glove.

11. A glove assembly, comprising:
    a glove;
    a support ring having an exterior surface; and
    a nozzle, coupled to the support ring, wherein a first portion of the nozzle is configured to connect to a source of compressed gas and a second portion of the nozzle retains the glove, and wherein the second portion comprises a plurality of orifices.

12. The glove assembly of claim 11, wherein the nozzle is coupled to the exterior surface of the support ring.

13. A method for donning a sterile glove, comprising:
    securing a cuff portion of a glove onto an opening of a vacuum chamber to establish a fluid-tight seal between the glove and the vacuum chamber;
    generating a vacuum in the vacuum chamber so as to inflate the glove;
    placing a hand in the inflated glove; and
    applying positive pressure to the cuff portion of the glove to release the glove from the opening of the vacuum chamber.

14. The method of claim 13, further comprising the step of:
    verifying the integrity of glove by observing the inflation of the glove prior to placing a hand in the glove.

15. A glove inflation apparatus, comprising:
    at least one vacuum chamber having an opening sized and shaped for receiving a glove; and
    a switch coupled to the vacuum chamber, a source of compressed gas, and a vacuum source, the switch having a first state and a second state, wherein in the first state the vacuum chamber is connected through the switch to the vacuum source, and in the second state the vacuum chamber is connected through the switch to the compressed gas source.

16. The glove assembly of claim 11, wherein the nozzle is annular.

17. The glove assembly of claim 11, wherein the nozzle is oval shaped.

\* \* \* \* \*